United States Patent
Kamihara et al.

(10) Patent No.: US 10,352,864 B2
(45) Date of Patent: *Jul. 16, 2019

(54) AUTOMATIC ANALYZER FOR IDENTIFYING A CAUSE OF ABNORMALITIES OF MEASUREMENT RESULTS

(75) Inventors: Kumiko Kamihara, Mito (JP); Satoshi Mitsuyama, Tokyo (JP); Tomonori Mimura, Kasama (JP); Chihiro Manri, Kawagoe (JP)

(73) Assignee: Hitachi High-Technologies Corporation, Tokyo (JP)

(*) Notice: Subject to any disclaimer, the term of this patent is extended or adjusted under 35 U.S.C. 154(b) by 1471 days.

This patent is subject to a terminal disclaimer.

(21) Appl. No.: 13/808,743

(22) PCT Filed: Jul. 4, 2011

(86) PCT No.: PCT/JP2011/065277
§ 371 (c)(1),
(2), (4) Date: Jan. 30, 2013

(87) PCT Pub. No.: WO2012/008324
PCT Pub. Date: Jan. 19, 2012

(65) Prior Publication Data
US 2013/0122596 A1    May 16, 2013

(30) Foreign Application Priority Data
Jul. 14, 2010    (JP) .................................. 2010-159995

(51) Int. Cl.
*G01N 35/00*    (2006.01)
*G01N 21/75*    (2006.01)
(Continued)

(52) U.S. Cl.
CPC .......... *G01N 21/75* (2013.01); *B01F 11/0266* (2013.01); *B01F 15/00214* (2013.01);
(Continued)

(58) Field of Classification Search
None
See application file for complete search history.

(56) References Cited

U.S. PATENT DOCUMENTS 9,476,893 B2 * 10/2016 Mitsuyama ...... G01N 35/00623
9,494,525 B2 * 11/2016 Tarumi ............... G01N 33/4905
2009/0222213 A1    9/2009 Hamazumi et al.

FOREIGN PATENT DOCUMENTS

JP    2004-347385 A    12/2004
JP    2005-181106 A    7/2005
(Continued)

OTHER PUBLICATIONS

International Preliminary Report on Patentability received in International Application No. PCT/JP2011/065277 dated Feb. 21, 2013.

*Primary Examiner* — Christopher Adam Hixson
*Assistant Examiner* — Michelle Adams
(74) *Attorney, Agent, or Firm* — Mattingly & Malur, PC (57) ABSTRACT

An automatic analyzer includes sample vessels containing samples to be measured and; reaction vessels in which to mix a sample and a reagent. A sample dispenser 5 dispenses a sample from any of the sample vessels to any of the reaction vessels. A reagent dispenser dispenses a reagent from a reagent vessel to a reaction vessel, and a stirrer stirs the sample-reagent mix contained in the reaction vessel. A photometric measurement unit is provided for obtaining multiple measurement data points during the progress of reaction of a mixed solution. At least one approximation formula is performed and an approximation curve from the measurement data points is generated. A shape descriptor is calculated from the approximation curve and abnormalities (Continued)

based on the shape descriptor are determined. This not only allows abnormalities to be detected accurately from each measurement result, but also allows the causes of the abnormalities to be identified.

5 Claims, 8 Drawing Sheets (51) Int. Cl.
*G16C 20/10* (2019.01)
*B01F 15/00* (2006.01)
*B01F 11/02* (2006.01)
*G01N 21/27* (2006.01)

(52) U.S. Cl.
CPC . *G01N 35/00594* (2013.01); *G01N 35/00623* (2013.01); *G01N 35/00663* (2013.01); *G16C 20/10* (2019.02); *G01N 21/272* (2013.01); *G01N 35/00603* (2013.01); *G01N 2035/0097* (2013.01); *G01N 2035/00465* (2013.01); *G01N 2035/00702* (2013.01); *Y10T 436/11* (2015.01)

(56) References Cited

FOREIGN PATENT DOCUMENTS

| JP | 2006-337125 A | 12/2006 |
| JP | 2009-204448 A | 9/2009 |
| JP | 2010-271095 A | 12/2010 |

* cited by examiner

AUTOMATIC ANALYZER FOR IDENTIFYING A CAUSE OF ABNORMALITIES OF MEASUREMENT RESULTS

TECHNICAL FIELD

The present invention relates to an automatic analyzer, an analysis method, and an information processor which are used to qualitatively and quantitatively analyze biological samples such as blood and urine.

BACKGROUND ART

In recent years, in automatic analyzers for performing qualitative and quantitative analyses on biological samples such as blood or urine, due to performance improvements, it has become possible to accurately analyze various items with a small amount of reagent or sample. On the other hand, the influence of factors influencing analysis accuracy, such as operational errors of each part of automatic analyzers and changes in the properties of reagents, is becoming large, and it is now required to maintain their status at normal range, detect the occurrence of abnormalities, and handle such problems properly.

As conventional techniques for detecting such abnormalities, for example, there are one in which reference temporal data created using a chemical reaction model is stored in advance, the reaction process data of a sample is compared against the reference temporal data, and an abnormality is detected when the difference is large (see Patent Document 1) and one in which absorbance changes are approximated by a function stored in advance, the actual absorbance changes measured are compared against the absorbance changes calculated from the function approximated, and an abnormality is detected based on the size of the difference (see Patent Document 2).

PRIOR ART DOCUMENT

Patent Document

Patent Document 1: JP-2004-347385-A
Patent Document 2: JP-2006-337125-A

SUMMARY OF THE INVENTION

Problem to be Solved by the Invention

However, in the above conventional technique, it is impossible to detect abnormal reactions other than those between the photometric measurement points used for concentration measurement and reaction changes in each measurement. Also, because the possible measurement range of the reagent used for analysis varies due to temporal changes in its properties, it has been difficult to sufficiently detect abnormalities from each measurement result. Further, because the causes of abnormalities will not be identified, it is possible that the reliability in reexamination after detection of an abnormality may decrease and the same abnormality may occur again.

Even if the operator confirms examination results and reaction processes, because the operator performs analyses on a great number of sample on a daily basis at the clinical site, it is extremely difficult to confirm all cases such as measurement results and reaction processes. Further, the problem with the confirmation by the operator is that the accuracy of abnormality detection and the accuracy of cause identification are dependent on the experience and skills of the operator.

The invention has been contrived to address the above the issues, and one object of the invention is to provide an automatic analyzer, analysis method and information processor which not only allow abnormalities to be detected accurately from each measurement result, but also allow the causes of the abnormalities to be identified.

Means for Solving the Problem

To achieve the above object, an automatic analyzer according to the invention comprises: a sample vessel for containing a sample to be measured; a reagent vessel for containing a reagent to be reacted with the sample; a reaction vessel in which to mix the sample and the reagent; a sample dispenser for dispensing the sample from the sample vessel into the reaction vessel; a reagent dispenser for dispensing the reagent from the reagent vessel into the reaction vessel; a stirrer for stirring the sample and the reagent contained in the reaction vessel to obtain a mixed solution; a measurement section for obtaining a plurality of measurement data points during the progress of reaction of the mixed solution; a storage section for storing one or more approximation formula to generate an approximation curve from the measurement data points; and a data processing section having a calculation section for selecting at least one approximation formula and generating an approximation curve from the measurement data points to calculate a shape descriptor from the approximation curve generated and an abnormality judgment section for performing abnormality judgment based on the shape descriptor.

Effect of the Invention

The invention not only allows abnormalities to be detected accurately from each measurement result, but also allows the causes of the abnormalities to be identified.

MODE FOR CARRYING OUT THE INVENTION

An embodiment of the present invention will now be described with reference to the accompanying drawings.

(1) Overall Structure of Automatic Analyzer

Figure 1:
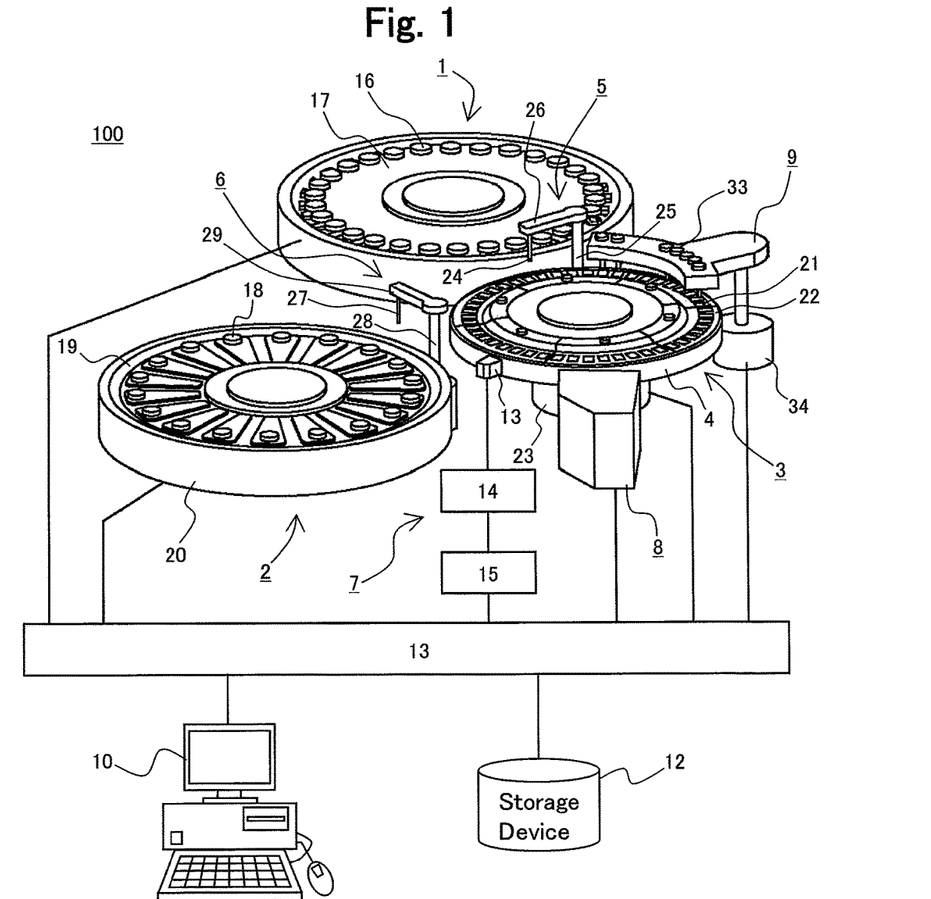
FIG. 1 is a diagram illustrating the overall structure of an automatic analyzer according to an embodiment of the invention.

FIG. 1 is a schematic of an automatic analyzer according to an embodiment of the invention.

The automatic analyzer 100 of FIG. 1 includes the following components: a sample disk 1, a reagent disk 2, a reaction disk 3, a sample dispenser 5, a reagent dispenser 6, a stirrer 7, a photometric measurement unit 8, (measurement section) a rinse mechanism 9, a storage device 12 (storage section), a controller 13, a computer 10 (PC), and the like. The sample disk 1 includes a circular disk 17 in which to store sample vessels 16 each containing a biological sample such as blood or urine. The reagent disk 2 includes a circular disk 19 in which to store reagent vessels 18. The reagent vessels 18 contain various reagents to be used for the analysis of the samples. The reagent disk 2 further includes a refrigerator 20 for maintaining the reagent vessels 18 at a constant temperature. The reaction disk 3 includes a reaction vessel holder 22 for holding reaction vessels 21 in which to mix a sample and a reagent. The reaction disk 3 further includes a reaction tank 4 for adjusting the temperatures of the reaction vessel 21 held by the reaction vessel holder 22. The reaction disk 3 is rotated by a drive mechanism 23. The sample dispenser 5 is designed to dispense a sample from any of the sample vessels 16 to any of the reaction vessels 21 and includes a support shaft 25, an arm 26, and a probe 24. The probe 24 is attached to the distal end of the arm 26 that can be rotated and vertically moved by the support shaft 25. The reagent dispenser is designed to dispense a reagent from any of the reagent vessels 18 to any of the reaction vessels 21 and includes a support shaft 26, an arm 29, and a probe 27. The probe 27 is attached to the distal end of the arm 29 that can be rotated and vertically moved by the support shaft 26. The stirrer 7 includes a stirrer controller 15 for controlling the vibration of a fixed unit 31 through the use of a piezoelectric driver 14 and is used to stir the mixed solutions within the reaction vessels 21. The photometric measurement unit 8 performs photometric measurement on any of the reaction vessels 21 when it passes through a light beam emitted from a light source (not illustrated), thereby detecting the absorbance of the mixed solution contained in that reaction vessel. The rinse mechanism 9 is used to clean the reaction vessels 21 after they have been subjected to photometric measurement. The rinse mechanism 9 includes nozzles 33 for suctioning and discharging rinse liquid and a lifter 34 for vertically moving the nozzles 33. The storage device 12 stores information such as analysis parameters, the number of times analysis can be done using each reagent bottle, the maximum number of times of analysis, calibration results, analysis results, and so forth. The controller 13 is used to control the entire operation of the analyzer 100.

The computer 10 has means for allowing input of information or commands into the controller 13 and means for displaying various pieces of information.

Figure 2:
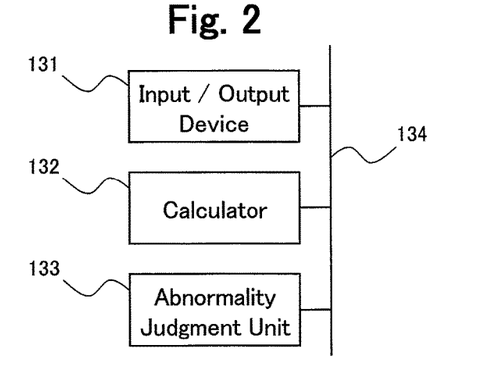
FIG. 2 is a diagram illustrating the functions of the controller of the automatic analyzer according to an embodiment of the invention.

FIG. 2 is a partial block diagram of the controller 13.

As illustrated in the figure, the controller 13 includes an input/output unit 131, a calculator 132 (calculation section), and an abnormality judgment unit 133. Data transfer can be done among these components via a data bus 134. The input/output unit 131 performs data transfer from/to the photometric measurement unit 8, the computer 10, and the storage device 12. The input/output unit 131, the calculator 132, and the abnormality judgment unit 133 can be implemented by hardware and CPUs. Alternatively, those components can be installed on a single CPU as software modules.

As discussed below, sample analysis performed by the analyzer 100 includes the following steps: sampling, reagent dispensing, stirring, photometric measurement, reaction vessel cleaning, and data processing (e.g., conversion of concentrations).

The sample disk 1 is controlled by the controller 13 via the computer 10. The sample vessels 16 are arranged along the circumference of the sample disk 1, and the sample disk 1 is rotated so that the sample vessels 16 can move to the position right below the probe 24 one after another according to the order of measurements. A given amount of the sample contained in a sample vessel 16 is dispensed into any of the reaction vessels 21 by a pump connected to the sample dispenser 5. The reaction vessel 21 that has received the sample then moves within the reaction tank 4 up to a first reagent dispensing position (i.e., the position below the probe 27). Thereafter, a given amount of the reagent contained in a reagent vessel 18 is dispensed into that reaction vessel 21 by a pump connected to the reagent dispenser 6. The reaction vessel 21 that has received the reagent moves to the position of the stirrer 7 where the first stirring is performed. The above steps are repeated until the same sample and several other reagents are mixed in the same reaction vessel 21. Once a reaction vessel 21 has been subjected to stirring, it passes through a light beam emitted from a light source, and the photometric measurement unit 8 (multi-wavelength photometer) detects the absorbance of the mixed solution in that reaction vessel 21. The resultant absorbance signal (absorbance data) is transmitted to the controller 13 where it is converted into the concentration of the sample. The controller 13 also performs abnormality judgment (discussed later) based on the absorbance. The absorbance data obtained before and after the conversion are stored on the storage device 12 and displayed on the screen of the computer 10. A reaction vessel 21 that has been subjected to photometric measurement is moved to the position of the rinse mechanism 9 and then cleaned for subsequent analyses.

In a two-wavelength measurement method involving the use of light of a wavelength that greatly changes in absorbance due to color changes resulting from reactions between a reagent and a sample (i.e., main wavelength) and light of a wavelength that hardly changes in absorbance (i.e., sub-wavelength), the difference between the absorbance of the main wavelength and the absorbance of the sub wavelength is input as absorbance data.

(2) Measurement Method in Clinical Assay

During reactions between a sample and a reagent, several absorbance measurements are done, and the resultant absorbance data is recorded as temporal data. This temporal data is also called reaction process data. Data confirmation in daily inspections is done using the reaction process data. Its method varies depending on the analysis method. Measurement methods in clinical assay can be roughly classified into the endpoint method and the rate method depending on the analysis method. The present embodiment illustrates an example in which the rate method is used, and the endpoint method is not discussed in detail herein.

(2-1) The Endpoint Method

In the endpoint method, the concentrations of the proteins and fat contained in a sample are measured. The amount of a substance generated by reactions between the substances in a sample and a reagent becomes closer to a particular value with the passage of time, and so do measurement values.

(2-2) The Rate Method

The rate method is used primarily to measure the activity values of the enzymes contained in a sample, not the concentrations of the enzymes. To perform the measurement, a given amount of a base is added as a reagent, and factors that change due to the consumption of the base by the enzymes are measured. The enzyme reaction rate becomes closer to a theoretical upper limit if the concentration of the base is relatively high. Reagents used for analysis of biological items contain a sufficient amount of a base. Thus, when a reaction between a sample and a reagent proceeds properly, reaction measurement values change linearly by a fixed amount with the passage of time.

Figure 3:
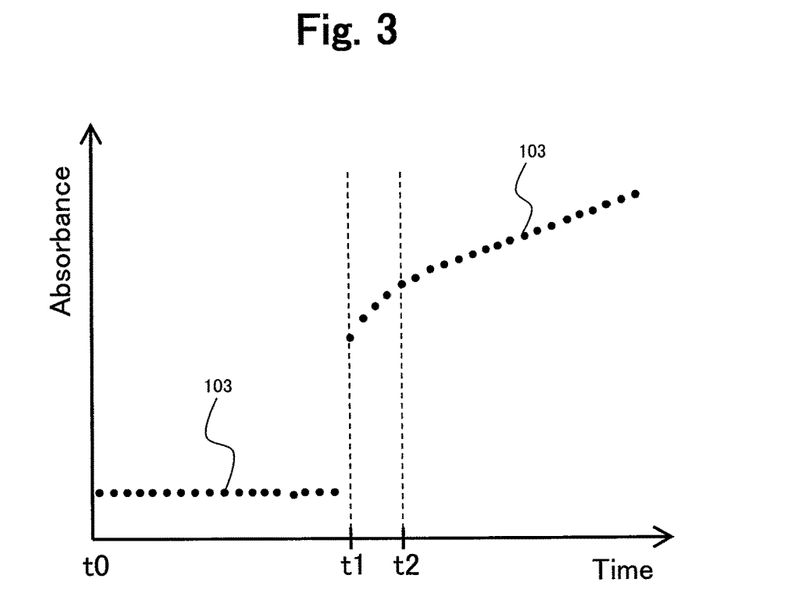
FIG. 3 is a diagram illustrating an example of the reaction process in the case of a two-reagent rate method and the reaction process in which absorbance increases.
Figure 4:
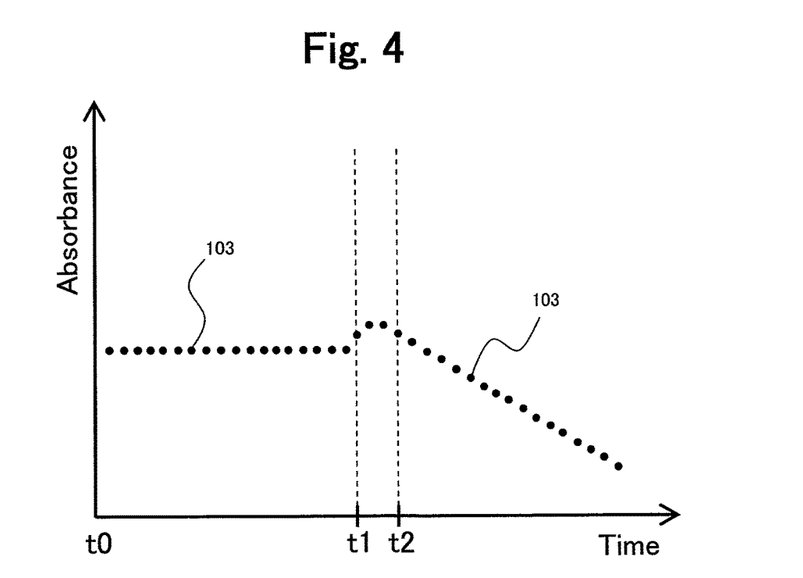
FIG. 4 is a diagram illustrating an example of the reaction process in the case of a two-reagent rate method and the reaction process in which absorbance decreases.

FIGS. 3 and 4 illustrate examples of reaction processes in which two reagents are used for the rate analysis. FIG. 3 shows a reaction process in which the absorbance increases while FIG. 4 shows a reaction process in which the absorbance decreases. In FIGS. 3 and 4, the horizontal axis represents time, the vertical axis represents the absorbance of the mixed solution inside a reaction vessel 21, and absorbance data 103 obtained at particular time intervals are plotted.

In the two-reagent method, the sample inside the reaction vessel 21 is mixed with a first reagent at time t0, followed by incubation at a proper temperature. During that time, sub-reactions and the like that do not influence the wavelength measured will proceed. At time t1 when the sub-reactions end, a second reagent is added and stirred for the main reaction to start, and the absorbance of the wavelength measured will change. The reaction process in such a rate method is influenced by the status of reactions between a sample and a reagent.

In the case of FIG. 3, the absorbance increases at time t1 when the main reaction starts, but the rate of this reaction does not always stay the same from the beginning and becomes almost constant after time t2 when the reaction is in a steady state. After time t2, the change rate (increase rate) of the absorbance becomes constant. That is, as illustrated in FIG. 3, the change status after time t2 takes the form of a straight line. Like this, the period between time t1 and time t2, i.e., from the start of the main reaction (time t1) to the steady state (time t2), is called a lag phase as a time lag.

The same is true of FIG. 4. That is, the absorbance increases after time t1 when the main reaction starts, but the rate of this reaction does not always stay the same from the beginning and becomes almost constant after time t2 when the reaction is in a steady state. After time t2, the change rate (increase rate) of the absorbance becomes constant. As illustrated in FIG. 3, the change status after time t2 takes the form of a straight line. The period between time t1 and time t2, i.e., from the start of the main reaction (time t1) to the steady state (time t2), is called a lag phase as time lag.

Figure 5:
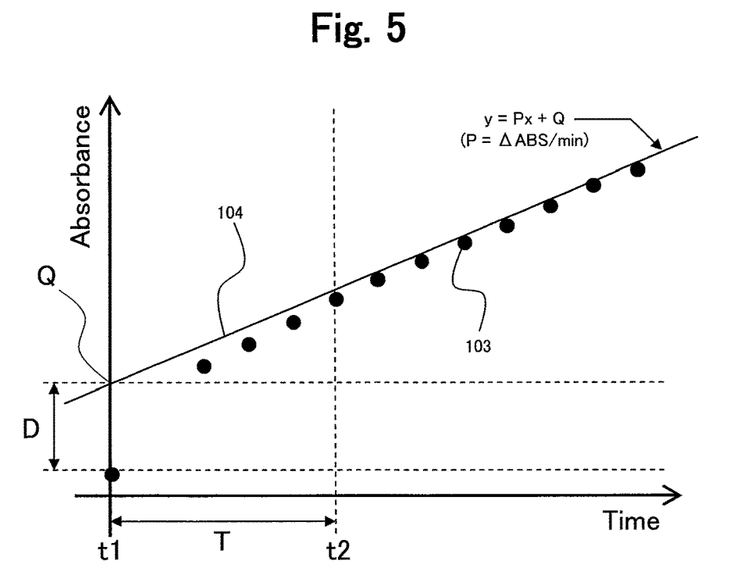
FIG. 5 is a diagram extracted from lag phase among the reaction process of FIG. 3.

The reaction process near a lag phase is further discussed below with reference to the accompanying drawings. Explained here is an example in which the absorbance increases with the progress of reaction as in FIG. 3. FIG. 5 is a graph extracted from the lag phase (time t1 to time t2) among the reaction process shown in FIG. 3.

Similar to FIG. 3, the horizontal and vertical axes of FIG. 5 represent time and the absorbance of the mixed solution inside a reaction vessel 21, respectively, and absorbance data 103 obtained at particular time intervals are plotted. Also, the length of the lag phase (time t1 to time t2) is T, an approximate straight line for the reaction process data after the end of the lag phase (time t2) is the straight line 104, the intersection point between the line showing time t1 (the absorbance axis of FIG. 5) and the line 104 is Q, and the difference between the absorbance at the intersection point Q and the absorbance at time t1 is D. At this time, when the slope of the line 104 is P (=ΔABS/min), the line 104 can be represented as y=Px+Q (y: absorbance variable, x: time variable).

Here, T, D, Q, and P are called shape descriptors as the indices representing the shape of reaction process data and hereinafter denoted by the shape descriptor T, shape descriptor D, shape descriptor Q, and shape descriptor P, respectively.

Possible factors that influence the accuracy of measurement results include the sampling mechanism, reagent dispenser, stirrer, optical system, reaction vessels, and thermostat bath of the analyzer. Measurement results are also influenced solely or in a combined manner by the composition or characteristics of reagents and samples. Reaction process data of the rate method has parts that distinctively show changes of such multiple influencing factors. The lag phase varies depending on analysis items, the composition of reagents, stirring status, reaction temperature, the concentration of the target substance in a sample, or the like. For example, γGT (γ-glutamyl transpeptidase), LD (lactate dehydrogenase), and the like have a relatively long lag phase while ALP (alkaline phosphatase), AST (aspartate amino transferase) have a short lag phase. This is because of differences in enzyme activity and because the number of conjugate enzymes or the liquid properties of reagents are different.

Like this, lag phases are influenced by various factors related to reaction, but the factors can be identified under certain conditions. We now describe the characteristics of reaction process data including lag phases and the relationship of factors that influence the characteristics.

(2-2-1) Size of a Lag Phase: Shape Descriptor D

As one example of the factors influencing the shape descriptor D, stirring status can be given. Stirring has the function of physically mixing a sample and a reagent and promoting their reaction. Thus, it seems that when stirring is done properly, the reaction between a sample and a reagent under the rate method reaches optimal conditions right after the stirring, and because the rate of the reaction becomes constant, the lag phase becomes short. On the other hand, when stirring is insufficient and the sample and the reagent have not been mixed sufficiently, a time lag occurs until the reaction rate reaches constant optimal conditions. Thus it can be said that the lag phase becomes large because the rate at which the absorbance during that time changes becomes slower. In other words, by using the lag phase size D shown in FIG. 5 as an index, the properties of the reaction between the sample and the reagent can be evaluated, and it also becomes possible to detect whether stirring has been done properly. When measurement is done for a certain item, it can be assumed that the influence of a reagent is always constant if the lot of the reagent is the same and the use period of the reagent is also the same. Further, reaction temperature is less likely to exhibit fluctuations in each measurement if the temperature of the thermostat bath is monitored. There is a constant relation between the concentration of the substance measured and the size of the lag phase, and it can be inferred that measurements that have deviated from the relation is due to insufficient stirring, that is, the status of the mixed solution is abnormal.

(2-2-2) Length of a Lag Phase: Shape Descriptor

As an example of the factors influencing the shape descriptor T, sample differences can be given. Since a lag phase is attributed to the reaction between a sample and a reagent, management of time until the lag phase becomes a steady reaction allows evaluation of the reaction status of that item. It seems that the length of a lag phase may also be influenced by other comprehensive factors such as a sample, a reagent, stirring, and reaction temperature. However, when measurement is done at a single institution, the composition of a generally used reagent is fixed, and reaction temperature, one of the device-related factors, will not change in each measurement. Thus, because the time T of a lag phase (the time between the start of the main reaction and a steady state) shown in FIG. 5 is influenced especially by the influence of reaction inhibitors or the like contained in the sample, monitoring of the time T of the lag phase allows detection of differences in sample properties and detection of abnormalities resulting from substances other than the substance to be measured such as reaction inhibitors.

(2-2-3) an Intercept of the Linear Equation (y=Px+Q) Obtained from Reaction Process Data Excluding the Lag Phase: Shape Descriptor Q As examples of the factors influencing the shape descriptor Q, reagent-related factors (deterioration and stability) and sample-related factors (lipemia, turbidity, or hemolysis) can be given.

(2-2-3.1) Deterioration and Stability of a Reagent

The intercept Q (shape descriptor Q) of the line 104 of FIG. 5 shows the absorbance at the time of the start of reaction at which a sample and a reagent are added. The value of this absorbance is not derived from the concentration of the target substance generated by the reaction between the sample and the reagent, but mostly reflects the absorption of the mixed solution between the first reagent and the second reagent and represents the absorbance of the reagent and the sample that are not dependent on the reaction generating the substance to be measured. As regards reagents of the rate method showing a reaction process in which the absorbance increases as in FIG. 3, one larger in absorption of the first reagent tends to be smaller in absorbance because the colored substances of the reagent are decomposed due to deterioration of the reagent. On the other hand, as regards reagents of the rate method showing a reaction process in which the absorbance decreases as in FIG. 4, absorption of the first reagent itself is low, but with the progress of reagent deterioration, the absorbance tends to be larger. The absorbance before the start of the main reaction is not dependent on the concentration of the target substance in the sample, but becomes almost constant. Thus, when the value of the shape descriptor Q of the data obtained by measuring the sample, control, and the like is monitored according to a temporal sequence, the value of the shape descriptor Q gradually decreases or increases along the temporal sequence with the progress of reagent deterioration. In other words, during calibration and measurement of a control sample, the quality of reagents cannot be confirmed in each measurement, but the use of this index allows confirmation of the quality of the reagents. Also, by setting a threshold for the value of the shape descriptor Q and by changing reagents based on the results of comparison against the threshold, the reagent change can be done before it influences measurement results, thereby preventing abnormalities of measurement results.

(2-2-3.2) Whitening, Turbidity, or Hemolysis of a Sample

In monitoring the value of the shape descriptor Q according to a temporal sequence, when the value changes discontinuously regardless of changes of reagent lots and bottles, it can be attributed to the influence of absorbance of the sample itself. As the sample, serum is often used, and to obtain a sample, peripheral blood collected in a blood collecting tube containing a blood separator is subjected to centrifugal separation, and serum is obtained from its upper layer. Depending on samples, there are ones that are hemolyzed during blood collection or the process of separation and serums that become white or opaque. Such samples may affect the absorbance depending on the wavelength used, and samples that have become white, opaque, or hemolyzed affect the results of measurement of items such as LD, AST, K (potassium), Fe (serum iron), TP (total protein), TTT (thymol turbidity test), and ZTT (zinc sulfate turbidity test). By monitoring the value of Q, whitening, turbidity, or hemolysis of samples can be detected.

(2-2-4) Slope of the Linear Equation (y=Px+Q) Obtained from Reaction Process Data Excluding the Lag Phase: Shape Descriptor P As examples of the factors including the shape descriptor P, factors related to the substance to be measured (concentration, activity values) and reagent-related factors (performance) can be given.

(2-2-4.1) Concentration and Activity Value of the Substance Measured

As one method of concentration calculation in the rate method, from the measurement values measured by using two standard solutions of two concentrations, when C2 is the concentration of a second standard solution, C1 is the concentration of a first standard solution, A2 is the absorbance of the second standard solution, and B is the absorbance of a blank standard solution, K factor (conversion coefficient) can be calculated from Formula 1 below.

$$K=(C2-C1)/(A2-B) \qquad \text{[Formula 1]}$$

Using this K factor, the value of the absorbance of the specified measurement point of a sample measured is typically converted into the concentration. The reaction process of the rate method obtained from each sample changes linearly within a given amount of time. The slope P of this line 104 represented by this linear equation (y=Px+Q) shown in FIG. 5 is the amount of change in absorbance per fixed time period; thus, by using this shape descriptor P, the concentration or activity value of the sample to be measured can be calculated.

(2-2-4.2) Evaluation of Reagent Performance

Reagents that use enzyme reaction have a sufficient amount of a base or enzyme so that there are no problems even if the target substance in a sample is high in concentration. However, the possible range of measurement of a reagent is limited, and as specified in its package insert, its linearity in fact fluctuates due to the temporal change of the reagent or lot differences. In the rate method, if within the possible range of measurement as the performance of the reagent, the concentration or activity value of the target substance in a sample and the amount of change in absorbance per fixed time period have a proportional relation of a linear equation. In other words, if outside the possible range of measurement as the performance of the reagent, the concentration or activity value of the target substance in the sample and the amount of change in absorbance per fixed time period are deviated from a proportional relation of a linear equation (i.e., linearity is lost). That is, by monitoring the shape descriptor P, it is possible to detect abnormalities related to the possible measurement range of a reagent such as the performance of the reagent (i.e., the range of the concentration that can be measured by that reagent), the abnormality in which the measurement has been done outside the possible measurement range of that reagent, or the absence of linearity in the possible measurement range specified in the package insert of that reagent (i.e., the possible measurement range in the package insert of the reagent is different from the actual possible measurement range). Further, since the shape descriptor P corresponds to the amount of absorbance change per fixed time period, by monitoring the relation between the measurement values of the sample and the shape descriptor P, the accuracy of the sample of those measurement values can be evaluated.

(3) Quantification of Shape Characteristics (Calculation of Shape Descriptors)

To quantitatively obtain the above-mentioned shape descriptors (T, D, Q, P) in reaction process data, the reaction process data is approximated by functions, and the resultant approximation curve is used to calculate the shape descriptors.

(3-1) Creating an Approximation Curve (Approximation Process)

In the present embodiment, as the functions to be used for approximation in which reaction process data is approximated (an approximation curve is created), formulas that can accurately approximate the lag phase (curved portion) that is the shape part characteristic of the reaction process of the rate method and the part (straight portion) in which reaction progresses steadily with fixed absorbance changes are used. The functions used for the approximate curve generation in the present embodiment are shown by Formulas 2 to 5. In the formulas that follow including Formulas 2 to 5, t represents time, and y absorbance. Also, a, b, c, d, e, k, p, q, r, u, v, and w are parameters.

$$y = a \times t + b + c \times exp(-k \times t) \quad \text{[Formula 2]}$$

$$y = a \times t + b + e/(t+d) \quad \text{[Formula 3]}$$

$$y = a \times t + b + e/(exp(u \times t) + v) \quad \text{[Formula 4]}$$

$$y = a \times t + b + p \times \log(1 + q \times exp(r \times t)) \quad \text{[Formula 5]}$$

Among these formulas, the function that can perform the most accurate approximation is selected, and when the reaction process data of the rate method is approximated, the value of each parameter (a, b, c, d, e, k, p, q, r, u, v, and w) is obtained. With the use of these parameters, the shape characteristics of the lag phase are quantified. Like this, by applying an approximation formula that can accurately reflect the shape changes of the reaction process obtained in each measurement, the sizes of theirs changes are quantified. By managing the values of the parameters quantified, the characteristics of each reaction can be known, and especially abnormal reactions that affect the accuracy of measurement results can be detected. In the present embodiment, from among the multiple approximation formulas representing the temporal changes of absorbance that can be stored on the storage device 12, the optimal approximation formula that is suited for the combination of the inspection items and the reagent is automatically determined and used.

A case in which approximation is performed using the above formula (Formula 3) is shown as an example and further explained in detail. When approximation is performed with the use of Formula 3, the values of the parameters in the formula are calculated such that the temporal absorbance change represented by an approximation curve generated and the actual temporal absorbance change become as small as possible. Specifically, the values of the parameters in the formula are calculated such that the square error between the absorbance data measured and stored and the absorbance calculated from the approximation formula becomes as small as possible. For the calculation of the values of the parameters, the existing least squares method is available, but as a method suitable for formulas of various forms, the parameters (a, b, e, d) that cause the square error to be the smallest are calculated by, for example, the steepest decent method. In reactions in which several reagents are used, after the reagent that causes the main absorbance change (normally the final reagent) is added, the absorbance starts to change greatly. In this case, only the data after the addition of the reagent that causes the main absorbance change is used for parameter calculation.

(3-2) Calculation of Shape Descriptors (T, D, Q, P)

Figure 6:
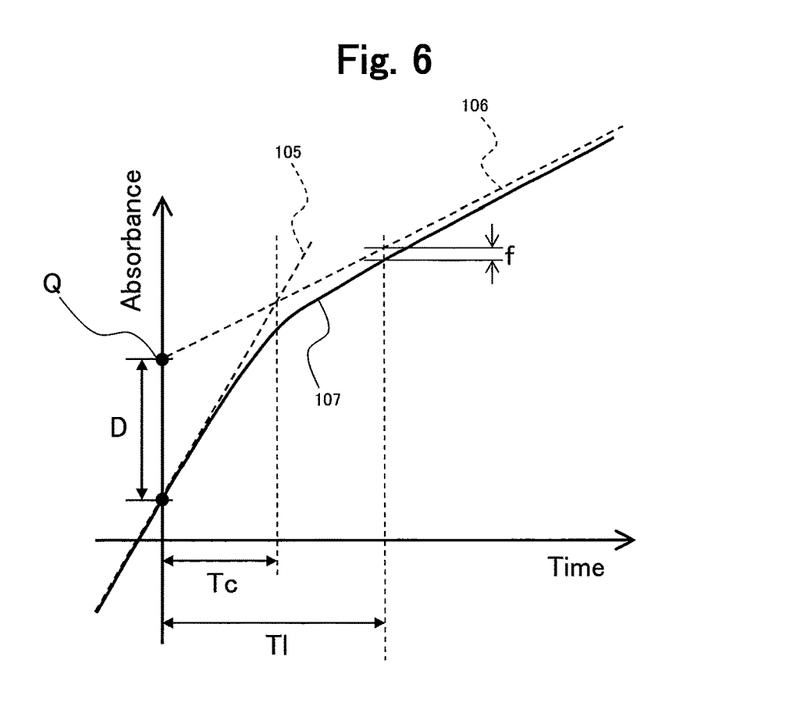
FIG. 6 is a diagram illustrating a case where an approximation curve is created using an approximation formula from reaction process data in the reaction process in which absorbance increases.

The process of calculating the shape descriptors (T, D, Q, P) from an approximation curve generated by the approximation process from reaction process data is explained with reference to FIG. 6. FIG. 6 is a diagram illustrating a case where an approximation curve 107 is created with the use of an approximation formula from the reaction process data in the reaction process in which the absorbance increases as in FIG. 5. The horizontal axis represents time, and the vertical axis the absorbance.

In FIG. 6, the line 105 (first line) is a tangent to the approximation curve 107 at the time of the start of the main reaction (right after the start), and the line 106 (second line) is a line to which the approximation curve is getting closer.

The time T1 at which the curve is sufficiently close is defined as the time at which the difference f between the approximation curve 107 and the line 106 at the same time becomes less than ε, which is a small value determined in advance. ε can be a fixed value or set according to the initial absorbance or the width of absorbance fluctuation. For example, the initial absorbance can be multiplied by a constant, or the difference between the initial absorbance and the last absorbance can be multiplied by a constant to obtain ε. To determine the time T1, a small value δ is determined, and the time TL can also be defined as the time at which the slope difference between the approximation curve 107 and the line 106 becomes less than δ. In this case, δ can be a constant or set according to the slope of the line 106. For example, the slope of the line 106 can be multiplied by a constant to obtain δ.

(3-2.1) Approximation Curve According to Approximation Formula (Formula 3)

For an approximation curve of such reaction process data, the shape descriptors are calculated using Formulas 6 through 10.

Shape descriptor D: the difference between the absorbance at the intersection between the absorbance axis (vertical axis) and the line 106 and the absorbance at the intersection between the absorbance axis (vertical axis) and the line 105

$$D = e/d \quad \text{[Formula 6]}$$

Shape descriptor T: the time shown by the intersection between the line 105 and the line 106 (Tc) or the time at which the line 106 and the approximation curve 107 is sufficiently close to each other (T1)

$$Tc=d \qquad \text{[Formula 7]}$$

$$T1=-d+(|e|/\varepsilon) \qquad \text{[Formula 8]}$$

Shape descriptor Q: the intersection between the absorbance axis (vertical axis) and the line 106 (intercept of the line 106)

$$Q=b \qquad \text{[Formula 9]}$$

Shape descriptor P: the slope of the line 106

$$P=a \qquad \text{[Formula 10]}$$

(3-2.2) Approximation Curve According to Approximation Formula (Formula 4)

When an approximation curve generated by an approximation formula (Formula 4) is used, the shape descriptors are calculated from Formulas 11 to 13 below.

Shape descriptor D: the difference between the absorbance at the intersection between the absorbance axis (vertical axis) and the line 106 and the absorbance at the intersection between the absorbance axis (vertical axis) and the line 105

$$D=w/(1+v) \qquad \text{[Formula 11]}$$

Shape descriptor T: the time shown by the intersection between the line 105 and the line 106 (Tc) or the time at which the line 106 and the approximation curve 107 is sufficiently close to each other (T1)

$$Tc=(1+d)/u \qquad \text{[Formula 12]}$$

$$T1=1/u\times\log(-v+|w|/\varepsilon) \qquad \text{[Formula 13]}$$

Shape descriptor Q: the intersection between the absorbance axis (vertical axis) and the line 106 (intercept of the line 106)

$$Q=b \qquad \text{[Formula 9]}$$

Shape descriptor P: the slope of the line 106

$$P=a \qquad \text{[Formula 10]}$$

(3-3) Data Evaluation Based on Shape Characteristics

Here, using the shape descriptors (D, T, Q, P) calculated from the reaction process data when measurement conditions (factors influencing the accuracy of measurement results) are changed, we now consider the evaluation of measurement data (measurement results) based on the shape characteristics.

(3-3.1) Evaluation of Measurement Data Using Shape Descriptor D

Figure 7:
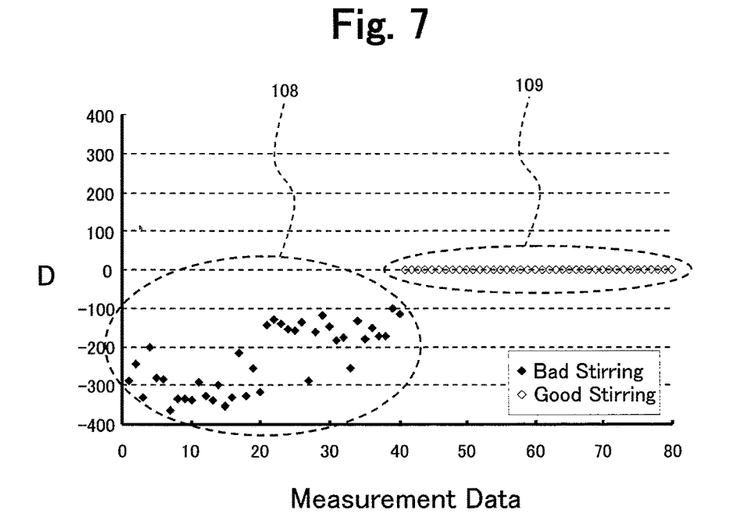
FIG. 7 is a diagram in which the shape descriptor D calculated using an approximation curve generated from reaction progress data about a sample measured under varied stirring conditions in measurement by γGT automatic analyzer is plotted.

FIG. 7 is a plotted diagram in which an approximation curve is generated from the reaction progress data about a sample measured under varied stirring conditions in measurement by a γGT automatic analyzer, with the vertical axis representing the shape descriptor D calculated from an formula (Formula 6) and the horizontal axis representing each reaction progress data. The shape descriptors D calculated using the reaction progress data when stirring failures occurred are arranged in 1 to 40 of the horizontal axis, and the shape descriptors D calculated using the reaction progress data when stirring has been done properly are arranged in 41 to 80 of the horizontal axis. It is obvious that as illustrated by a group of data 108, the absolute value of the shape descriptor D when a stirring failure occurred is large, and as illustrated by a group of data 109, the absolute value of the shape descriptor D when stirring has been done properly is small. Thus, from the values of the shape descriptor D, stirring status can be evaluated.

(3-3.2) Evaluation of Measurement Data Using Shape Descriptor T

Figure 8:
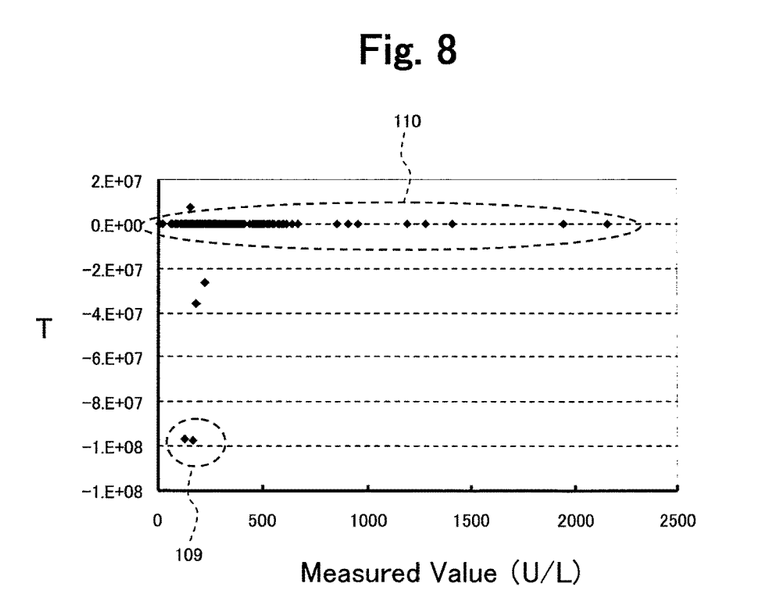
FIG. 8 is a diagram in which the shape descriptor T calculated about measurement item LD is plotted.

FIG. 8 is a plotted diagram in which the vertical axis represents the shape descriptor T (T1) calculated using a formula (Formula 13) about measurement results of LD and the horizontal axis represents measurements values (U/L) calculated from the apparatus. As illustrated by a data group 110, as regards LD, the shape descriptor T shows the value of 0 about almost all the measurement results regardless of the sizes of the measurement values. This means that the time of the lag phase is small. However, several data as illustrated by a data group 109 show large absolute values of T1, and it can be judged that this is due to the reaction specific to the sample because this data is not related to the temporal sequence.

(3-3.3) Evaluation of Measurement Data Using Shape Descriptor Q

Figure 9:
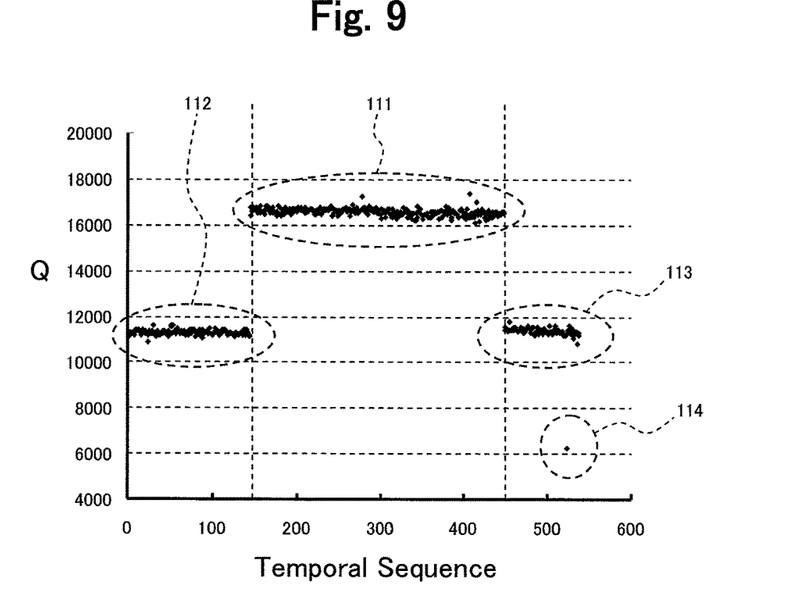
FIG. 9 is a diagram in which the shape descriptor Q calculated about measurement item LD is plotted.

FIG. 9 is a plotted diagram in which the vertical axis represents the shape descriptor Q calculated using a formula (Formula 9) about measurement item LD and the horizontal axis represents a temporal sequence. As illustrated by a data group 111, only the values of the shape descriptor Q in a certain temporal sequence are higher than other data groups 112, 113. This coincides with the time of sample measurement and the day of reagent bottle replacement, and it can be detected that the values of the shape descriptor Q are due to reagent bottle differences. Also, in data (group) 114, the value of the shape descriptor Q is small in only one measurement regardless of the temporal sequence, and it seems that this is due to hemolysis of the sample.

(3-3.4) Evaluation of Measurement Data Using Shape Descriptor P

Figure 10:
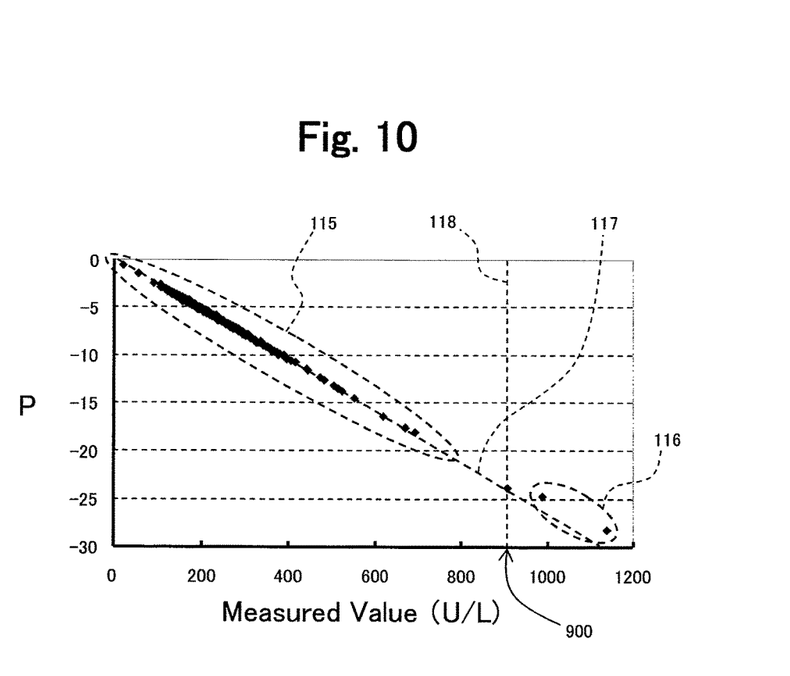
FIG. 10 is a diagram in which the shape descriptor P calculated by measuring a general sample is plotted.

FIG. 10 is a plotted diagram in which the horizontal axis represents the shape descriptor P calculated using a formula (Formula 10) by measuring a general sample and the horizontal axis represents measurement values (U/L) calculated from the apparatus. A data group 115 is on a line 117, but it deviates from the line 117 when the measurement value (U/L) exceeds 900 (U/L). From this data, it can be seen that the possible measurement range of the reagent used at this measurement is up to the measurement value shown by a line 118 or thereabout (in this example, up to a measurement value of 900 U/L), and for the measurement of the two points of a data group 116 that show measurement values larger than that, amount-reduced re-examination is necessary.

(4) Abnormality Judgment

Figure 11:
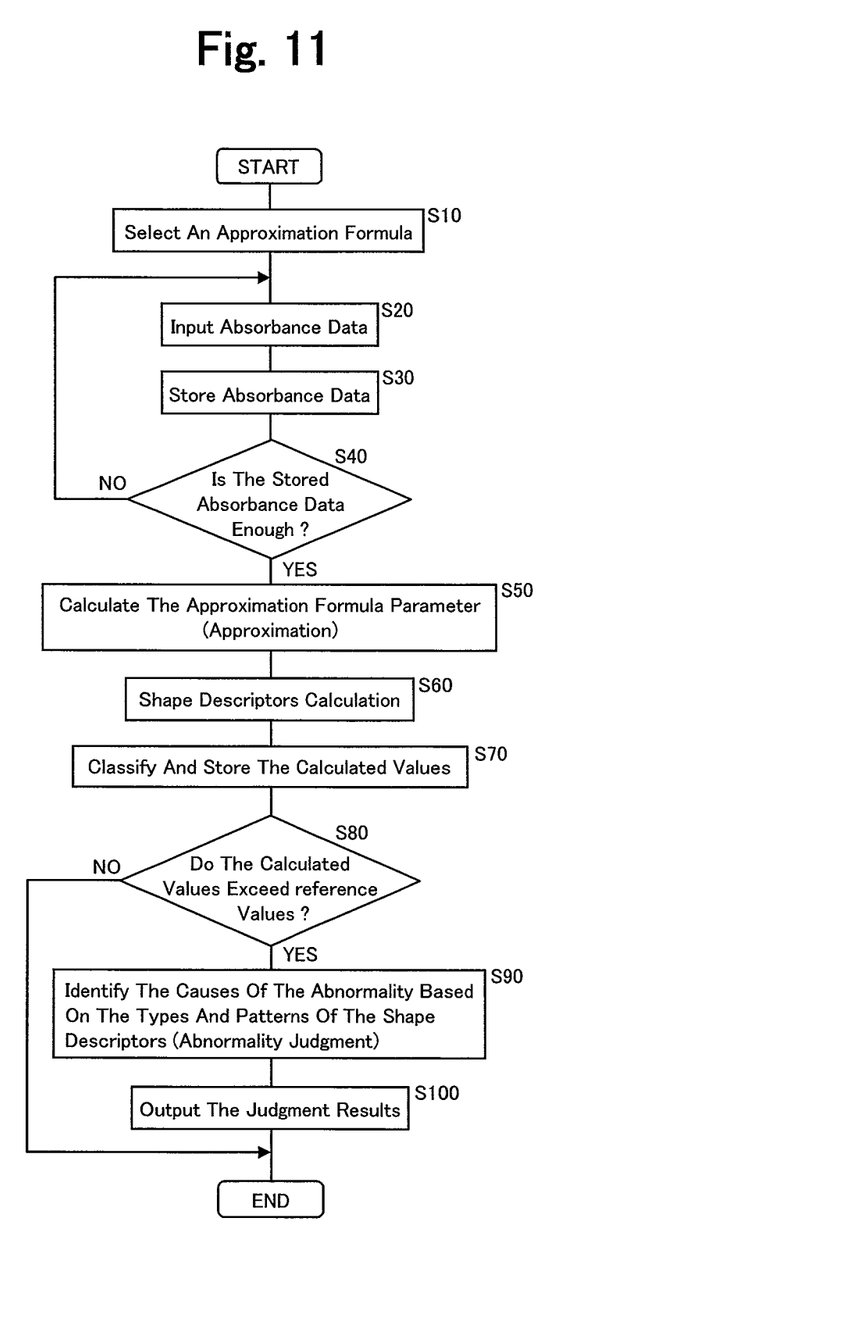
FIG. 11 is a flowchart illustrating the content of abnormality judgment according to one embodiment of the invention.

We now explain about the content of the abnormality judgment performed at the controller 13 in the present embodiment with reference to the accompanying drawings. FIG. 11 is a flowchart illustrating the content of the abnormality judgment of the present embodiment, and FIG. 12 is a tree diagram illustrating the content of the abnormality cause judgment in the abnormality judgment.

In the abnormality judgment shown in FIG. 11, the controller 13 first selects an optimal approximation formula from among one or more approximation formulas stored on the storage device 12 based on the combination of inspection items and reagents (Step S10). Next, by the input/output unit 131, the absorbance data of one measurement or the average of several measurements of the absorbance measured several times with the passage of time is input from the photometric measurement unit 8 to the controller 13 (Step S20), and the input absorbance data is stored on the storage device 12 (Step S30). Then, whether the absorbance data necessary for subsequent steps has been stored is judged (Step S40), and when the judgment result is NO, the process returns to Step S20, followed repetition of Steps S20 and 30 until the judgment result becomes YES. Also, when the judgment results in Step S40 is YES, by the calculator 132, the parameters of the approximation formula are calculated (approximation process) such that the temporal change of the absorbance represented by the approximation formula selected in Step S10 and the temporal change of the actual absorbance are as small as possible (Step S50). Next, by the calculator 132, the shape descriptors (T, D, Q, P) showing the characteristics of the absorbance change pattern of the part in which the absorbance of the earlier stage of the main reaction changes in a curved manner are calculated (Step S60), and the calculated shape descriptors are classified according to the types and stored on the storage device 12 (Step S70). Then, whether or not the calculated shape descriptors exceed reference values (for example, a range defined by upper and lower limit values) pre-stored on the storage device 12 is judged (Step S80), and when the judgment result is YES, an abnormality cause judgment (described later) in which the causes of the abnormality are judged from the types and patterns of the shape descriptors is performed (Step S90), followed by the transfer of the judgment result from the abnormality judgment unit 133 to the computer (PC) 10 (Step S100), Also, when the judgment result in Step S80 is NO, the process ends.

Figure 12:
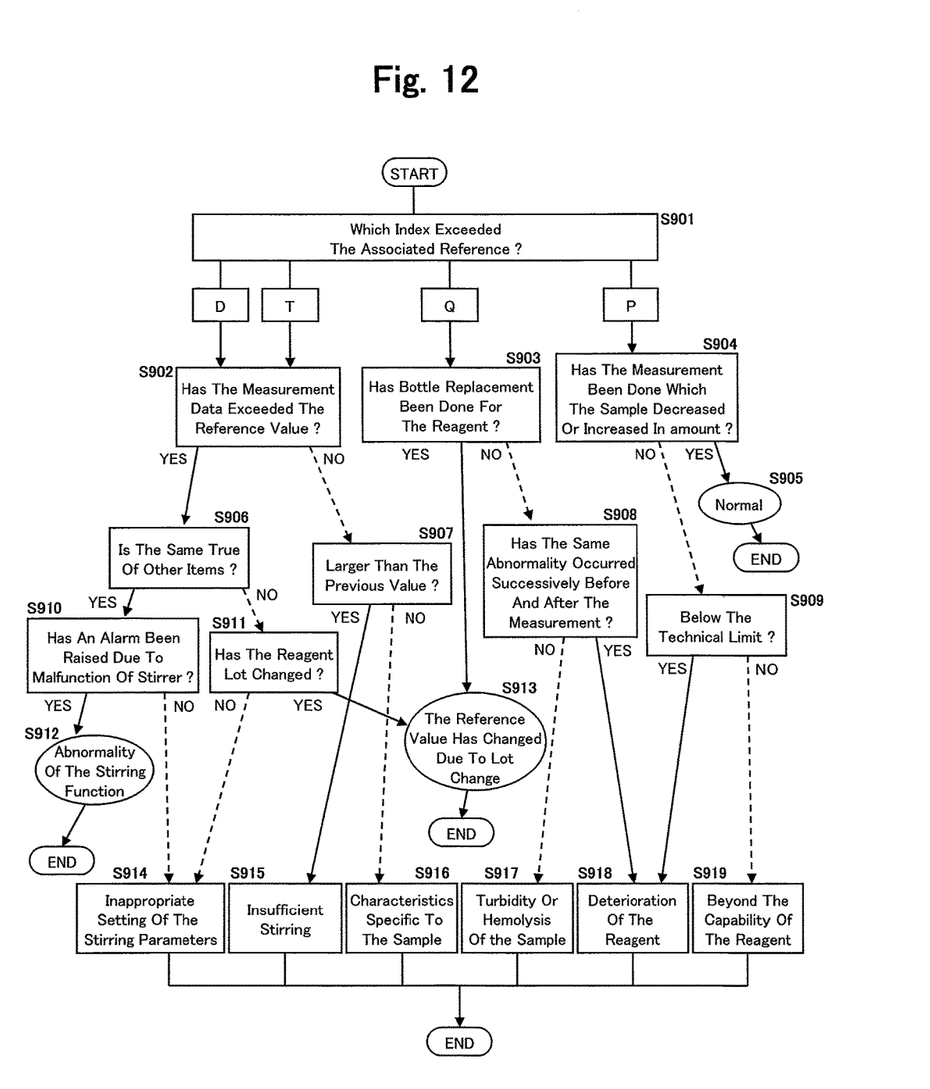
FIG. 12 is a tree diagram illustrating the content of abnormality cause judgment according to one embodiment of the invention.

In the abnormality judgment shown in FIG. 12, the controller 13 first judges what is the type of the index (shape descriptor) that exceeded the reference values (Step S901).

In Step S901, when the index that exceeded the reference value is the shape descriptor D or T, whether the measurement data exceeds the reference data in a continuous manner is judged (Step S902). When the judgment result is YES, whether the same occurred in other items (Step 906) and whether a data alarm of the stirring function has been issued (Step S910) are judged. When the judgment results are both YES, the stirring function is judged abnormal (Step S912), and the process ends. Further, when the judgment result in Step S910 is NO, the stirring parameter setting is judged bad (Step S914), and the process ends. When the judgment result in Step S906 is NO, whether the reagent lot has been changed is judged (Step S911), and when the judgment result is No, the stirring parameter setting is judged bad (Step S914), and when the judgment result is YES, it is judged that the reference value has changed due to lot change (Step S913), and the process ends. Also, when the judgment result in Step S902 is NO, whether the value is larger than the previous value is judged (Step S907), and when the judgment result is YES, stirring is judged insufficient (Step S915), and when the judgment result is NO, it is judged that sample singularity is responsible (Step S916), and the process ends.

In Step S901, when the index that exceeded the reference value is the shape descriptor Q, whether reagent bottle replacement has been done is judged (Step S903), and when the judgment result is YES, it is judged that the reference value has changed due to lot change (Step S913), and the process ends. Also, when the judgment result in Step S903, whether the same has occurred continuously before and after the measurement is judged (Step S908), and when the judgment result is NO, it is judged that the turbidity or hemolysis of the sample is responsible (Step S917), and when the judgment result is YES, it is judged that reagent deterioration is responsible (Step S918), and the process ends.

In Step S901, when the index that exceeded the reference value is the shape descriptor Q, whether the sample has been subjected to amount-increased or amount-decreased measurement is judged (Step S904), and when the judgment result is YES, it is judged that the absorbance data is normal (Step S905), and the process ends. Further, when the judgment result in Step S904 is NO, whether the absorbance data is within the range of the technical limit is judged (Step S909), and when the judgment result is YES, it is judged that reagent deterioration is responsible (Step S918), and when the judgment result is NO, it is judged that the absorbance data is outside the range of reagent performance (Step S919), and the process ends.

We now discuss the operation in the present embodiment thus configured.

Sample analysis performed by the analyzer 100 includes the following steps: sampling, reagent dispensing, stirring, photometric measurement, reaction vessel cleaning, and data processing (e.g., conversion of concentrations).

When the automatic analyzer 100 starts an analysis, the sample disk 1 is controlled by the controller 13 via the computer 10. The sample vessels 16 are arranged along the circumference of the sample disk 1, and the sample disk 1 is rotated so that the sample vessels 16 can move to the position right below the probe 24 one after another according to the order of measurements. A given amount of the sample contained in a sample vessel 16 is dispensed into any of the reaction vessels 21 by a pump connected to the sample dispenser 5. The reaction vessel 21 that has received the sample then moves within the reaction tank 4 up to a first reagent dispensing position (i.e., the position below the probe 27). Thereafter, a given amount of the reagent contained in a reagent vessel 18 is dispensed into that reaction vessel 21 by a pump connected to the reagent dispenser 6. The reaction vessel 21 that has received the reagent moves to the position of the stirrer 7 where the first stirring is performed. After the reaction vessel 21 has been subjected to addition of all necessary reagents and stirring, it passes through a light beam emitted from a light source, and the photometric measurement unit 8 (multi-wavelength photometer) detects the absorbance of the mixed solution in that reaction vessel 21. The resultant absorbance signal (absorbance data) is transmitted to the controller 13 where it is converted into the concentration of the sample. The controller 13 also performs abnormality judgment based on the absorbance. The absorbance data obtained before and after the conversion are stored on the storage device 12 and displayed on the screen of the computer 10. Absorbance data that has been judged abnormal during the abnormality judgment is displayed on the screen of the computer 10 together with possible causes identified, thereby prompting the operator to take proper actions (e.g., elimination of the abnormality causes or reanalysis). When the photometric measurement is complete, the reaction vessel 21 is moved to the position of the rinse mechanism 9 and then cleaned for subsequent analyses.

We now discuss the effects in the present embodiment thus configured.

In the conventional technique for detecting abnormalities of measurement results in an automatic analyzer, it is impossible to detect abnormal reactions other than those between the photometric measurement points used for concentration measurement and reaction changes in each measurement. Also, because the possible measurement range of the reagent used for analysis varies due to temporal changes in its properties, it has been difficult to sufficiently detect abnormalities from each measurement result. Further, because the causes of abnormalities will not be identified, it is possible that the reliability in reexamination after detection of an abnormality may decrease and the same abnormality may occur again. Even if the operator confirms examination results and reaction processes, because the operator performs analyses on a great number of sample on a daily basis at the clinical site, it is extremely difficult to confirm all cases such as measurement results and reaction processes. Further, the problem with the confirmation by the operator is that the accuracy of abnormality detection and the accuracy of cause identification are dependent on the experience and skills of the operator.

On the other hand, in the preset embodiment, it is configured such that an approximation curve is created from measurement data points, and shape descriptors are calculated from the approximation curve, and abnormality judgment is performed based on the shape descriptors. Thus, it is possible to sufficiently detect abnormalities from each measurement result, and it is also possible to identify the causes of the abnormalities.

Not only are a control and a calibrator evaluated, but it is also possible to evaluate each measurement result of patient samples of unknown concentrations. It is also possible to assure the reliability of measurement data from the data of the control.

Further, about factors in which apparatus abnormalities influence reaction process data, it is possible to check the abnormalities from daily inspection data and contribute to the maintenance of apparatus performance.

Moreover, in a sample of a known concentration such as a control sample and a standard solution, calculation and monitoring of changes in reaction process curves allows the temporal performance of the stirrer to be checked. Thus, it is possible to detect the halt of stirring and changes in reaction rates, making it possible to actively notify the apparatus user of the necessity of stirrer maintenance and replacement from the side of the automatic analyzer.

Further, the presence or absence or level of stirring for which evaluation is vague can be quantified; thus, it is possible to verify and determine optimal parameters for each item and each reagent in addition to abnormality detection for the stirrer.

Because the slowness of reaction can be quantified, and because reaction abnormalities can be detected from changes in reaction rates when reagents deteriorate or when dilution occurs due to the rinse liquid inside the reagent probe, it is possible to detect reagent deteriorations caused by human errors in daily inspections and prevent overlooking wrong data output.

In the present embodiment, we have described examples in which abnormality judgment is performed by the controller 13 that has an input/output unit, a calculator, an abnormality judgment unit, and the like, but the invention is not limited to this. For example, it is possible to perform abnormality judgment by installing an input/output unit, a calculator, an abnormality judgment unit, and the like on the inside of the computer softwarewise.

Figure 13:
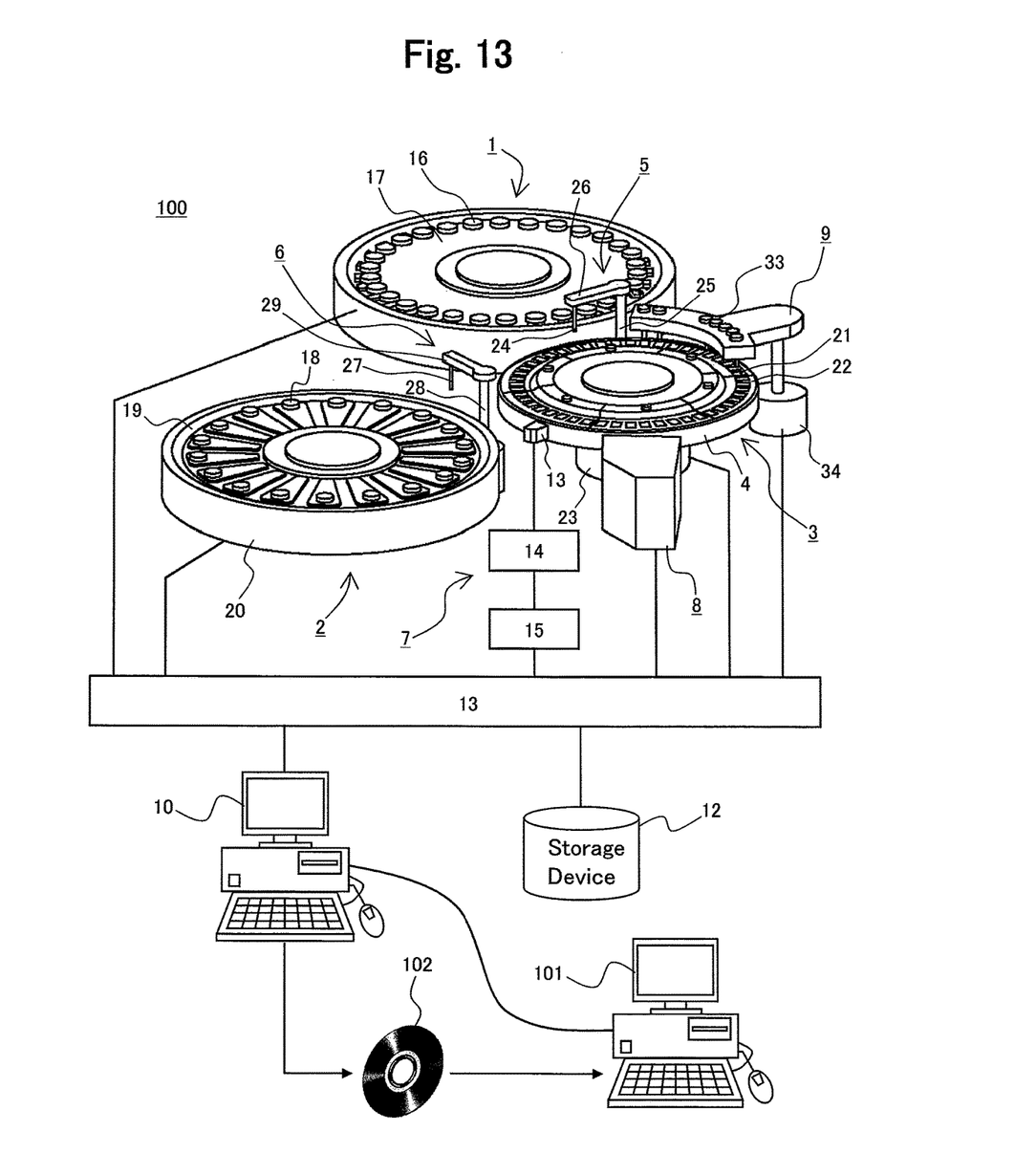
FIG. 13 is a diagram illustrating an information processor according to one embodiment of the invention.

Also, as in FIG. 13, it is instead possible to perform abnormality judgment by installing softwarewise an input/output unit for reaction process data, a calculator, an abnormality judgment unit, and the like on the inside of an external computer (PC) 101 that exists separately and independently of the automatic analyzer. That is, the data obtained from the automatic analyzer can be calculated by an information processor that exists separately and independently of the automatic analyzer. In this case, this information processor includes a storage device for storing one or more approximation formulas used to generate an approximation curve from measurement data points, a calculator for selecting at least one approximation formula to generate an approximation curve from multiple measurement data points, thereby calculating the shape descriptors from the approximation curve generated, and a data processor having an abnormality judgment unit for performing abnormality judgment using the shape descriptors. Multiple measurement data points in the reaction process of a mixes solution are output from the automatic analyzer. In this case, the measurement data points (reaction process data) output from the automatic analyzer can be transferred by connecting the automatic analyzer and the external computer via a LAN. It is also possible to store the data on an external output medium such as a CD-R, DVD-RAM, or the like and transfer the data to the external computer (information processor) via such a medium, and analyze the data. As for the details of information processing, it is the same as the functions of the information processing in the automatic analyzer already described, and an explanation about this is skipped.

Also, we have described examples in which Formula 3 is used as an approximation formula, but the invention is not limited to this. It is possible to use Formulas 2, 4, 5, and in that case, it is needless to say that the same effects can be obtained.

DESCRIPTION OF REFERENCE NUMERALS

1: Sample disk
2: Reagent disk
3: Reaction disk
4: Reaction tank
5: Sample dispenser
6: Reagent dispenser
7: Stirrer
8: Photometric measurement unit
9: Rinse mechanism
10: Computer (PC) with display
11: Input unit
12: Storage device
13: Controller
14: Piezoelectric driver
15: Stirrer controller
16: Sample vessel
17, 19: Circular disk
18: Reagent bottle
20: Refrigerator
21: Reaction vessel
22: Reaction vessel holder
23: Drive mechanism
24, 27: Probe
25: Support shaft
26, 29: Arm
28: Support shaft
31: Fixed unit
33: Nozzle
34: Lifter
51: Input/output unit
52: Calculator
53: abnormality judgment unit
54: Storage device
55: Data bus
100: Automatic analyzer
101: External computer (information processor)
102: External output medium

The invention claimed is:

1. An automatic analyzer comprising:
a sample vessel containing a sample to be measured;
a reagent vessel containing a reagent to be reacted with the sample;
a reaction vessel;
a sample dispenser to dispense the sample from the sample vessel into the reaction vessel;
a reagent dispenser to dispense the reagent from the reagent vessel into the reaction vessel;
a stirrer to stir the sample and the reagent contained in the reaction vessel to obtain a mixed solution;
a photometer which obtains a plurality of measurement data points during progress of a reaction of the mixed solution;
a storage device storing one or more approximation formulas to generate an approximation curve from the measurement data points; and
a processor connected to a memory storing instructions that, when executed by the processor, cause the processor to be configured to select one of the one or more approximation formulas, generate an approximation curve from the measurement data points and the selected approximation formula, calculate one or more shape descriptors from the generated approximation curve, and perform an abnormality cause judgment to identify a cause of abnormalities of measurement results based on the one or more shape descriptors;
wherein the calculated one or more shape descriptors include at least one of shape descriptor T and shape descriptor D, and
wherein, a tangent to the generated approximation curve right after a start of the reaction is a first line and a line approaching the generated approximation curve is a second line, the shape descriptor T is a time at which the first line and the second line intersect, and the shape descriptor D is a difference between the first line and the second line at the start of the reaction.

2. The automatic analyzer of claim 1,
wherein the calculated one or more shape descriptors include the shape descriptor T, and
wherein the abnormality cause judgment judges a cause of abnormalities of measurement results based on the shape descriptor T.

3. The automatic analyzer of claim 2,
wherein the abnormality cause judgment judges that the abnormalities result from substances other than a target substance in the sample based on the shape descriptor T.

4. The automatic analyzer of claim 1,
wherein the calculated one or more shape descriptors include the shape descriptor D, and
wherein the abnormality cause judgment judges a cause of abnormalities of measurement results based on the shape descriptor D.

5. The automatic analyzer of claim 4,
wherein the abnormality cause judgment judges that the abnormalities are caused by the mixed solution based on the shape descriptor D.

* * * * *